United States Patent [19]
Storz

[11] 3,995,287
[45] Nov. 30, 1976

[54] ENDOSCOPIC CAMERA

[76] Inventor: Karl Storz, auf dem Schildrain 39, D-72 Tuttlingen, Germany

[22] Filed: May 3, 1974

[21] Appl. No.: 466,637

[52] U.S. Cl. .................................. 354/62; 354/225
[51] Int. Cl.² ................... G03B 17/48; G03B 13/02
[58] Field of Search ............................. 354/62, 225

[56] References Cited
UNITED STATES PATENTS

| | | | |
|---|---|---|---|
| 2,284,562 | 5/1942 | Dittmann | 354/225 |
| 3,257,902 | 6/1966 | Hopkins | 354/62 |

Primary Examiner—L. T. Hix
Attorney, Agent, or Firm—Eugene M. Eckelman

[57] ABSTRACT

An endoscope shaft directs its rays into a camera lens and a shutter is provided to control exposure of film to the rays. At least two viewfinders are arranged in spaced relation for viewing by two or more persons simultaneously, and movable beam splitting prisms in the paths of the rays deflect rays from the lens into the viewfinders for the simultaneous viewing by the two or more persons.

2 Claims, 3 Drawing Figures

ENDOSCOPIC CAMERA

The invention relates to an endoscopic camera, particularly a mirror reflex camera wherein the path of the rays through the camera lens firstly passes onto a hinged mirror in front of the film to be exposed which deflects the path of the rays approximately at right angles into a prismatic viewfinder. Just before the photograph is taken the mirror is moved up and closes the prismatic viewfinder, the camera shutter is triggered, and the film is exposed.

It has long been known to use such cameras for endoscopic purposes in that they permit the making of a photographic record for documentation purposes of what is seen through the endoscope. Preferably cameras with a mirror reflex attachment are used. A mechanism on endoscopes with a source of light has proved particularly suitable, whereby the light source is arranged separately from the endoscope and is connected with the latter by means of a per se known flexible light conductor located in the area outside the endoscope (German Patent 1,113,788). Only as a result of this was it in fact possible to use large powerful light sources both for research and for kinematographic or television purposes without the ease of handling of the endoscope or the treatment of the patient being impaired.

In training doctors it is also known to use so-called joint observation systems in endoscopy, whereby several persons can observe simultaneously the image in the cavity of the internal organs. However, the considerable disadvantage is then encountered that only the joint observation system or the camera can be mounted on the endoscope. Therefore, observation by the doctor being trained is interrupted during the photographic process so that in this connection training is deficient. Furthermore, the interchange of the joint observation system and camera is cumbersome and time-consuming.

The problem of the invention is therefore to obviate this disadvantage and to so improve the camera of the type described hereinbefore that joint observation is possible through the camera itself without interchanging parts.

According to the invention, this problem is solved in that one or more additional partially permeable prisms are arranged in the path of the rays of the camera by means of which a split off path is passed to one or more joint observation eye-pieces.

In this way a joint observation system can be associated with the known mirror reflex attachment so that the endoscopic expert himself observes through the viewfinder of the mirror reflex attachment and at least one further person, for example the doctor being trained, can simultaneously observe the setting of the object to be photographed through the joint observation system. As a result, continuous joint observation and photography at any time during the endoscopic process are possible without the cumbersome interchanging of camera and joint observation system.

According to a further development of the invention, the partially permeable prism or prisms located on a sliding guide can be moved out of the path of the rays just before taking the photograph.

It can also be advantageous to arrange one or more additional mirrors in the split off path of the rays. Sometimes it is simpler to use fixed mirrors than prisms. Two partially permeable juxtaposed prisms can also be constructed as a unit and can therefore be moved jointly out of the path of the rays.

In general, the joint observation system can be fitted at various points in the radiation path. In the case of a single-lens mirror reflex camera with a hinged mirror, the existing viewfinder prism is advantageously constructed as a partially permeable prism and the transmitted pencil of rays is then conducted with a corresponding spacing onto a second prism or onto a mirror which represents a second viewfinder prism for the observer. In fact it is also possible to construct this second viewfinder prism as a partially permeable prism, and to conduct the transmitted pencil of rays into a third viewfinder prism. Naturally, however, the image in the third viewfinder is not as bright as in the first two viewfinders. This construction naturally has the advantage that no movement of the prisms is necessary, and that the complete focusing hood can in known manner be closed by the mirror prior to exposure quite independent of the number of viewfinders connected.

Further advantages and details of the invention can be gathered from the following description of two embodiments with reference to the drawings, wherein.

Figure 1:
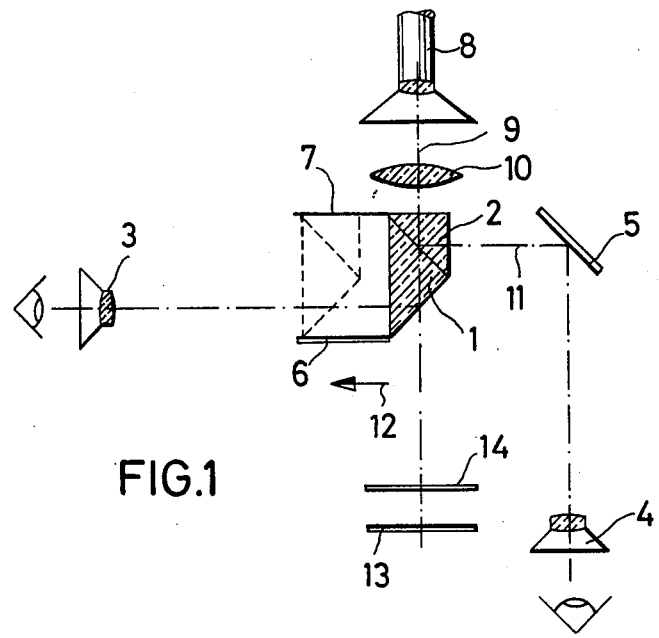
FIG. 1 is a diagrammatic view showing an arrangement of a first embodiment.

FIG. 1 shows the endoscope shaft 8 through which the pencil of rays 9 penetrates the lens 10 of the camera and enters the first partially permeable prism 2. From there part 11 of the pencil of rays is conducted to mirror 5 and from there into the eye-piece 4 of the viewfinder. A further partially permeable prism 1 is constructed as a unit with partially permeable prism 2; the non-reflected part of the pencil of rays 9 enters prism 1 and is deflected into the eye-piece 3 of the observer.

This arrangement has the advantage that the two viewfinders 3 and 4 are arranged at right angles to one another.

If the shutter button of the camera is now operated the unit comprising the two prisms 1 and 2 in sliding guides 6 and 7 is moved under the action of a spring, not shown in the direction of arrow 12 until it assumes the position shown by broken lines on the left-hand side, wherein the path of the rays can reach film 13 in unimpeded manner as soon as the shutter 14 opens in a known manner. This takes place at the time in which the unit with prisms 1 and 2 reaches the extreme left-hand position and then triggers shutter 14 in known manner. The details are not shown because they are well known to the skilled expert.

If the light source is sufficiently powerful, it is also possible to leave the prism unit 1,2 in the position represented in FIG. 1 during exposure because both prisms 1 and 2 are partially permeable.

Figure 2:
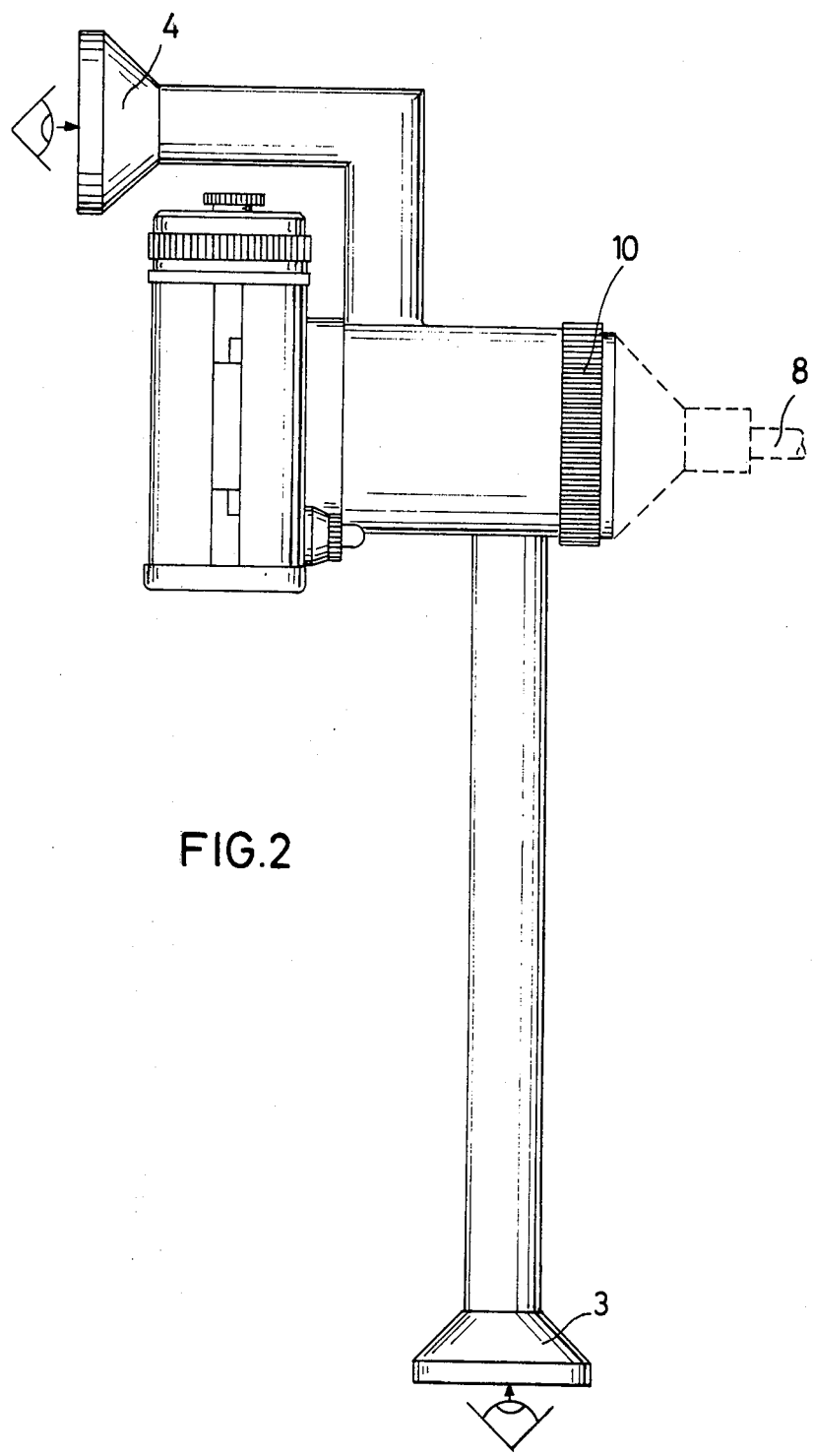
FIG. 2 is a side view of a camera according to the invention.

FIG. 2 shows an external view of the embodiment of FIG. 1 whereby the endoscope shaft 8 is represented in broken lines. As lens 10 is generally interchangeable it can be used without the remainder of the camera, provided that the latter is not required.

Figure 3:
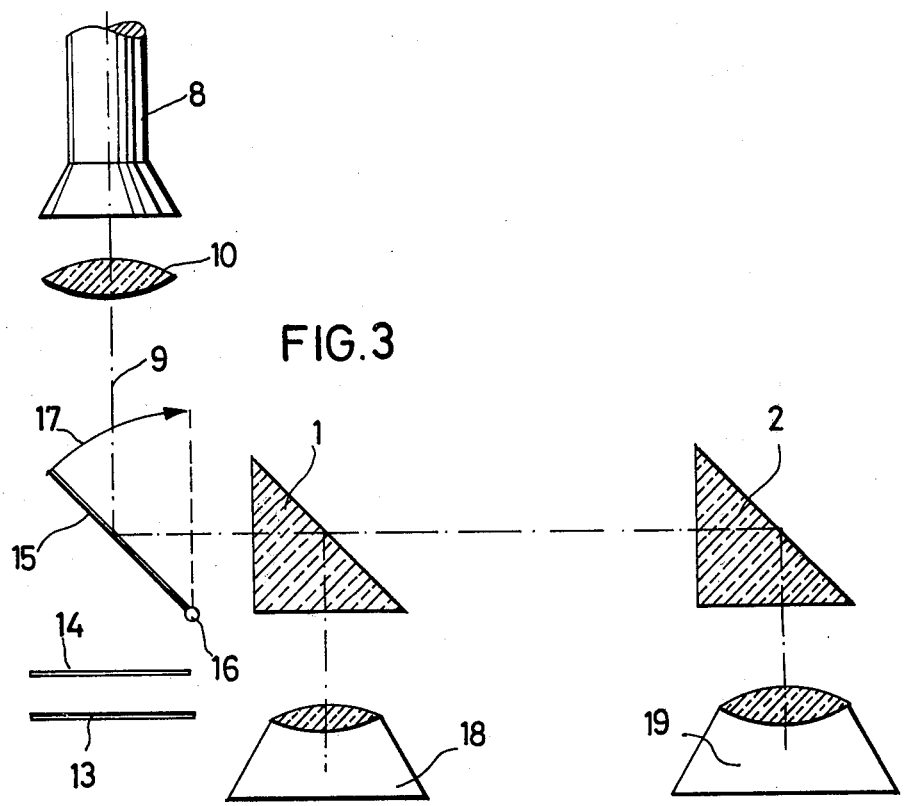
FIG. 3 is a diagram of a second embodiment.

FIG. 3 shows a more advanced embodiment with a single lens mirror reflex camera. In this case mirror 15 can be moved about fulcrum point 16 in the direction of arrow 17 in order to release the radiation path 9 for exposing film 13 by shutter 14. This is already known per se. According to the invention prism 1 of viewfinder 18 is partially permeable so that only about 50% of the light leak can be deflected into viewfinder 18, whilst the remainder passes into the second prism 2 from where it is reflected into viewfinder 19. It is also possible to use a mirror in place of the second prism 2. Naturally the two viewfinders 18 and 19 are so spaced relative to one another that two persons can easily observe the image. As in this way the focusing hood can become relatively long, it can be made disassemblable for ease of transportation.

The invention is not restricted to the two indicated embodiments. For example, in FIG. 3 a third viewfinder (not shown) can be connected for a second observer, although naturally the light intensity is then reduced. In addition, very varied arrangements can be provided within the scope of the invention.

I claim:

1. An endoscopic camera comprising a housing, an endoscope shaft on said houing directing its rays into the latter, a camera lens in said housing arranged to receive the rays from said endoscope shaft, shutter means in said housing arranged to control exposure of film to said rays, at least two viewfinders on said housing arranged such that they can be viewed by different persons at the same time, and a pair of beam splitting prisms in said housing in the path of said rays deflecting said rays into said viewfinders for the simultaneous viewing by the two or more persons, said beam splitting prisms being supported on a slidable guide whereby to be movable out of the path of the rays for taking the photograph.

2. The endoscopic camera of claim 1 wherein said pair of prisms are constructed into a single unit.

* * * * *